United States Patent
Beilfuss et al.

(10) Patent No.: US 10,584,283 B2
(45) Date of Patent: Mar. 10, 2020

(54) PRESERVATIVE FOR TECHNICAL PRODUCTS

(71) Applicant: Schülke & Mayr GmbH, Nordestedt (DE)

(72) Inventors: Wolfgang Beilfuss, Hamburg (DE); Ralf Gradtke, Tornesch (DE); Jennifer Knopf, Hamburg (DE)

(73) Assignee: VINK CHEMICALS GMBH & CO. KG, Kakenstorf (DE)

( * ) Notice: Subject to any disclaimer, the term of this patent is extended or adjusted under 35 U.S.C. 154(b) by 0 days.

(21) Appl. No.: 16/061,827

(22) PCT Filed: Dec. 13, 2016

(86) PCT No.: PCT/EP2016/080746
§ 371 (c)(1),
(2) Date: Jun. 13, 2018

(87) PCT Pub. No.: WO2017/102696
PCT Pub. Date: Jun. 22, 2017

(65) Prior Publication Data
US 2018/0362845 A1    Dec. 20, 2018

(30) Foreign Application Priority Data
Dec. 14, 2015   (DE) .......... 10 2015 121 692

(51) Int. Cl.
C09K 15/30   (2006.01)
A01N 43/647  (2006.01)
A01N 35/02   (2006.01)
C09K 15/02   (2006.01)
C09K 15/20   (2006.01)
C23F 11/14   (2006.01)

(52) U.S. Cl.
CPC ............. C09K 15/30 (2013.01); A01N 35/02 (2013.01); A01N 43/647 (2013.01); C09K 15/02 (2013.01); C09K 15/20 (2013.01); C23F 11/149 (2013.01)

(58) Field of Classification Search
CPC ........ A01N 33/04; A01N 33/08; A01N 59/00; A01N 35/02; A01N 43/647; C09K 15/02; C09K 15/20; C09K 15/30; C23F 11/149
See application file for complete search history.

(56) References Cited

U.S. PATENT DOCUMENTS

| | | |
|---|---|---|
| 2004/0082473 A1 | 4/2004 | Beilfuss et al. |
| 2005/0218379 A1 | 10/2005 | Beilfuss et al. |
| 2011/0046140 A1 | 2/2011 | Brutto et al. |
| 2015/0041411 A1 | 2/2015 | Gradtke et al. |

FOREIGN PATENT DOCUMENTS

| | | |
|---|---|---|
| DE | 229 707 | 11/1985 |
| DE | 280 536 | 7/1990 |
| DE | 102 44 442 | 4/2004 |
| DE | 10 2004 014 447 | 10/2005 |
| DE | 10 2012 203 003 | 8/2013 |
| EP | 0 347 815 | 12/1989 |
| JP | 2002-069045 A | 3/2002 |
| RO | 108290 | 4/1994 |

OTHER PUBLICATIONS

International Search Report and Written Opinion for corresponding PCT/EP2016/080746, dated Jan. 20, 2017.
Office Action issued in Brazilian Patent Application No. BR112018011870-2 dated Sep. 18, 2019 with English translation provided.
Paulus, Wilfried, "Directory of Microbicides for the Protection of Materials," 2004, selected excerpts.

*Primary Examiner* — Mark Kopec
*Assistant Examiner* — Jaison P Thomas
(74) *Attorney, Agent, or Firm* — YOUNG & THOMPSON

(57) ABSTRACT

The invention relates to a preparation comprising a) 10 to 80% by weight of α,α',α"-trimethyl-1,3,5-triazine-1,3,5-(2H,4H,6H) triethanol (TTT) and b) one or more additives selected from i) ammonia, ii) alkanolamines with primary amino group and alkyl group having at most eight carbon atoms and iii) alkylamines with primary amino group and alkyl group having at most eight carbon atoms, where the weight ratio a):b) is in the range from 100:30 to 100:1. The preparation is present as semi-concentrate and has an advantageously lower viscosity, is moreover storage-stable, in particular storage-stable over a long period.

15 Claims, No Drawings

PRESERVATIVE FOR TECHNICAL PRODUCTS

CROSS REFERENCE TO RELATED APPLICATIONS

This application is a 371 of International Application PCT/EP2016/080746, filed Dec. 13, 2016, which claims priority to German Patent Application No. 10 2015 121 692.2, filed Dec. 14, 2015, the entire contents of which are incorporated herein by reference.

BACKGROUND

The invention relates to a preparation with a content of α,α',α"-trimethyl-1,3,5-triazine-1,3,5-(2H,4H,6H)triethanol. The preparation is formulated as semi-concentrate. The invention further relates to the use of the preparation for the preservation of water-based products and processes.

The product Grotan® WS (Schilke & Mayr GmbH, Norderstedt, Federal Republic of Germany) comprises about 80% by weight of the formaldehyde depot compound α,α',α"-trimethyl-1,3,5-triazine-1,3,5-(2H,4H,6H)triethanol (N,N',N"-tris(2-hydroxypropyl) hexahydrotriazine, hereinbelow TTT). TTT is prepared by condensation of 1-aminopropan-2-ol (monoisopropanolamine, MIPA) with formaldehyde (in the molar ratio 1:1). The condensation product is a colourless to yellow liquid which is storage-stable and has a shelf life of more than 36 months.

The composition has good bactericidal action, a broad, balanced activity spectrum (including sulphate-reducing bacteria), good instantaneous action, good anticorrosive properties and is free of nitrate, nitrosating agents and organically bonded chlorine (thus does not contribute to the AOX value).

A disadvantage of the concentrate is the high viscosity of the product, in particular at low temperature. Although dilute TTT solutions can be prepared, namely i) from Grotan® WS by dilution with water, ii) by reaction of aqueous MIPA solution with paraformaldehyde or iii) by reaction of MIPA with formalin solution, the water-diluted solution and the preparation in diluted form unfortunately have the disadvantage that the solution assumes an intense red colour upon storage and, in contrast to the highly concentrated Grotan® WS, is not storage-stable. In general, the stability decreases with increasing dilution. A low-viscosity preparation with an advantageously high content of TTT and with improved stability is therefore sought.

DE 102 44 442 A1 discloses low-emission formaldehyde depot preparations with a content of a) at least one formal and b) at least one emission-reducing additive selected from urea, urea derivatives, amino acids, guanidine and guanidine derivatives, with certain specific active ingredients being excluded.

DE 10 2004 014 447 A1 describes N-formal-containing preservatives which also comprise emission-reducing additives selected from urea, urea derivatives, amino acids, guanidine and guanidine derivatives, and monoethylene glycol.

DE 10 2012 203 003 A1 describes liquid preparations for the reduction of free oxygen in industrial waters. The preparation comprises a) N-formal, b) dialkylhydroxylamine, and optionally c) antioxidant and d) alkalizing agent. The intended amount of alkalizing agent is high and is said to ensure that a sufficiently alkaline pH is maintained in the use dilution because this improves the action of the diethylhydroxylamine used as oxygen scavenger.

According to the teaching of EP 0 347 815 A2, alkanolamines are used for the stabilization of triazine derivatives. In this connection, the additional presence of surfactants is obligatorily prescribed. The surfactants used in the examples, however, are poorly biodegradable. It was therefore also an object of the present invention to provide preparations with a content of formaldehyde depot compound in which the use of surfactants is not obligatory.

Surprisingly, it has now been found that these objects are achieved by a preparation which comprises:
a)—10 to 80% by weight of α,α',α"-trimethyl 1,3,5-triazine 1,3,5-(2H,4H,6H)triethanol (TTT) and
b)—One or more additives selected from
i.—Ammonia,
ii.—Alkanolamines with primary amino group and alkyl group having at most eight carbon atoms and
iii.—Alkylamines with primary amino group and alkyl group having at most eight carbon atoms,
where the weight ratio a):b) is in the range from 100:30 to 100:1.

SUMMARY

The invention is based inter alia on the fact that it has been found that the active ingredient stability and the colour stability of a TTT solution diluted with water is considerably improved if selected additives or stabilizers are added. A preferred stabilizer is MIPA. In this connection, it is of no significance whether the stabilizer (e.g. the alkanolamine) is added before or after the condensation. Thus, if a slightly increased amount of amino alcohol is used for the reaction of formaldehyde with MIPA (molar ratio of 1:1), then the stability of a water-based, more dilute, low viscosity Grotan® WS solution is improved.

Examples of alkylamines with primary amino group and alkyl group having at most eight carbon atoms are alkylamines of the formula $R^a NH_2$, where $R^a$ is a linear or branched alkyl group, preferably ethylamine, propylamine, butylamine and hexylamine.

Here, preference is given to a preparation in which the presence of N,N-dialkyl hydroxylamine of the formula RR'NOH, where R and R' are selected independently from linear, branched and cyclic $C_1$- to $C_{10}$-alkyl groups, is excluded, where the N,N-dialkyl hydroxylamine whose presence is preferably excluded in the preparation is N,N-diethyl hydroxylamine (DEHA).

A preferred weight ratio a):b) is in the range from 100:25 to 100:1.5, preferably in the range from 100:20 to 100:2, in particular in the range from 100:15 to 100:2.5, such as 100:13 to 100:5.

Preferably, the fraction of a) TTT is in the range from 10 to 80% by weight, more preferably 13 to 75% by weight, in particular 16 to 70% by weight, for example 20 to 65% by weight.

It is also preferred that component b) comprises one or more additives selected from i) ammonia and ii) alkanolamines with primary amino group and alkyl group with at most eight carbon atoms. The preparation thus comprises:
a)—10 to 80% by weight of α,α',α"-trimethyl 1,3,5-triazine-1,3,5-(2H,4H,6H)triethanol (TTT) and
b)—One or more additives selected from
i.—Ammonia,
ii.—Alkanolamines with primary amino group and alkyl group having at most eight carbon atoms, where the weight ratio a):b) is in the range from 100:30 to 100:1.

DESCRIPTION OF PREFERRED EMBODIMENTS

Alkanolamines used according to the invention are preferably selected from 1-aminopropan-2-ol (isopropanolamine), 3-aminopropanol (propanolamine), 2-amino ethanol (monoethanolamine), 2-amino-2-methylpropanol (aminomethylpropanol) and 4-aminobutanol (butanolamine), where the alkanolamine is preferably isopropanolamine.

In a first particularly preferred embodiment, component b) is ammonia. The preparation thus comprises:

a)—10 to 80% by weight of α,α',α"-trimethyl-1,3,5-triazine-1,3,5-(2H,4H,6H)triethanol (TTT) and b)—Ammonia, where the weight ratio a):b) is in the range from 100:30 to 100:1.

In a second preferred embodiment, component b) consists of one or more alkanolamines. The preparation thus comprises:

a)—10 to 80% by weight of α,α',α"-trimethyl-1,3,5-triazine-1,3,5-(2H,4H,6H)triethanol (TTT) and b)—One or more alkanolamines with primary amino group and alkyl group having at most eight carbon atoms.

In this embodiment, component b) is preferably isopropanolamine.

Moreover, the invention relates to the use of the preparation for the preservation of technical products and processes. The technical product is particularly preferably selected from cooling lubricant concentrates and emulsions, with an application for the preservation of water-mixed cooling lubricants being particularly preferred according to one embodiment of the invention.

According to a preferred embodiment, no isothiazolin-3-one is present in the preservative according to the invention as is obligatory according to the teaching of DE 10 2004 052 878 A1.

To improve the fungicidal action, pyridine-2-thiol 1-oxide sodium salt can be added.

The advantages of the present invention arise in particular from the examples below. All quantitative data refer to the weight, unless stated otherwise.

EXAMPLES

Materials Used:

Grotan® WS (Schilke & Mayr GmbH, Norderstedt, Federal Republic of Germany), which comprises about 80% by weight of the formaldehyde depot compound α,α',α"-trimethyl-1,3,5-triazine-1,3,5-(2H,4H,6H)triethanol (TTT);

GLUCOPON 215 UP (BASF SE, Ludwigshafen, Federal Republic of Germany) which is a preservative-free, aqueous solution of alkyl polyglucosides based on natural $C_{8-10}$-fatty alcohol.

Experiment 1

A 50% strength solution of Grotan® WS in water was prepared, which thus corresponds to 40% by weight of TTT in water:

| Zero value | |
|---|---|
| Appearance | clear, yellowish |
| Colour number Hazen/Gardner | 14/0.0 |
| Density g/ml at 20° C. | 1.0545 |
| Refraction at 20° C. | 1.4032 |
| Cleavable HCHO % | 13.6 |

Samples of this solution were stored in bottles made of polyethylene at −5° C., 25° C. and 40° C. in order to investigate the stability.

| 1.5 months | −5° C. | 25° C. | 40° C. |
|---|---|---|---|
| Appearance | clear, yellowish | slightly opal, pale yellow, haziness at the bottom | clear, intense yellow |
| Colour number Hazen/Gardner | n.d. | 83/0.3 | ***/5.4 |
| Density g/ml at 20° C. | n.d. | 1.0541 | 1.0532 |
| Refraction at 20° C. | n.d. | 1.4030 | 1.4028 |
| Cleavable HCHO % | n.d. | 13.4 | 12.6 |

| 3 months | −5° C. | 25° C. | 40° C. |
|---|---|---|---|
| Appearance | clear, yellowish | clear, yellow | clear, orange |
| Colour number Hazen/Gardner | 27/0.0 | 234/1.3 | ***/8.5 |
| Density g/ml at 20° C. | 1.0548 | 1.0539 | 1.0526 |
| Refraction at 20° C. | 1.4034 | 1.4030 | 1.4029 |
| Cleavable HCHO % | 13.4 | 13.2 | 11.4 |

| 6 months | −5° C. | 25° C. | 40° C. |
|---|---|---|---|
| Appearance | clear, yellowish | clear, yellow | clear, red |
| Colour number Hazen/Gardner | 31/0.1 | 852/4.2 | ***/12.0 |
| Density g/ml at 20° C. | n.d. | 1.0536 | 1.0522 |
| Refraction at 20° C. | n.d. | 1.4030 | 1.4035 |
| Cleavable HCHO % | n.d. | 12.3 | 8.9 | n.d.—not determined.

| 12 months | −5° C. | 25° C. | 40° C. |
|---|---|---|---|
| Appearance | clear, pale yellow | clear, dark yellow | clear, red |
| Cleavable HCHO % | 13.1 | 11.4 | 5.22 |

Experiment 1 shows that the aqueous dilution of TTT is not storage-stable, particularly at elevated temperature and over a period of 12 months (which simulates storage over a long period).

Experiment 2

Experiment 2 was carried out with a condensation product prepared from the starting materials 1-aminopropan-2-ol and formaldehyde (and specifically in the form of paraformaldehyde).

| Raw materials | Parts by weight |
|---|---|
| Demineralised Water | 50 |
| 1-aminopropan-2-ol | 34.74 |
| Paraformaldehyde 91% | 15.26 |
| Total | 100 |

A three-neck flask with CPG stirrer and condenser was charged with water and 2-hydroxypropylamine was added with stirring. Then, paraformaldehyde was added in portions such that a temperature of 70° C. was not exceeded (if necessary cooling). When the addition was complete, the mixture was stirred for one hour at 60-70° C. until the paraformaldehyde had completely dissolved.

| Zero value | |
|---|---|
| Appearance | clear, colourless |
| Colour number Hazen/Gardner | 13/0.0 |
| Density g/ml at 20° C. | 1.0546 |
| Refraction at 20° C. | 1.4030 |
| Cleavable HCHO % | 13.5 |

Samples of this solution were stored in bottles made of polyethylene at −5° C., 25° C. and 40° C. in order to test the stability.

| 1st month | −5° C. | 25° C. | 40° C. |
|---|---|---|---|
| Appearance | clear, colourless | clear, pale yellow | clear, intense yellow |
| Colour number Hazen/Gardner | 13/0.0 | 60/0.2 | ***/5.3 |
| Cleavable HCHO % | n.d. | 13.1 | 12.2 |

| 3rd month | −5° C. | 25° C. | 40° C. |
|---|---|---|---|
| Appearance | clear, yellowish | clear, yellow | clear, orange |
| Density g/ml at 20° C. | 1.0545 | 1.0537 | 1.0527 |
| Refraction at 20° C. | 1.4030 | 1.4029 | 1.4031 |
| Colour number Hazen/Gardner | 11/0.0 | 337/2.0 | ***/9.2 |
| Cleavable HCHO % | 13.4 | 12.9 | 11.0 |

| 6 months | −5° C. | 25° C. | 40° C. |
|---|---|---|---|
| Appearance | clear, yellowish | clear, yellow | clear, orange |
| Cleavable HCHO % | n.d. | 12.3 | 8.4 |

| 12 months | −5° C. | 25° C. | 40° C. |
|---|---|---|---|
| Appearance | clear, yellowish | clear, orange | slightly cloudy, neck in, brown-red |
| Cleavable HCHO % | 13.2 | 11.4 | 4.6 |

| 18 months | −5° C. | 25° C. | 40° C. |
|---|---|---|---|
| Appearance | clear, yellowish | clear, red-orange | slightly cloudy, neck in, brown-red |
| Cleavable HCHO % | 13.4 | 10.9 | 2.38 | n.d. = not determined.

The condensation product prepared from paraformaldehyde is thus also not storage-stable.

Experiment 3

Experiment 2 was carried out using a condensation product prepared from the starting materials 1-aminopropan-2-ol and formaldehyde (in the form of paraformaldehyde). In experiment 3, formalin solution (32% formaldehyde) was used instead.

| | A/parts | B/parts |
|---|---|---|
| 1-aminopropan-2-ol | 75.11 | 75.11 |
| Formaldehyde solution | 93.75 | 89.06 |
| Molar ratio | 1:1 | 1.053:1 |

1-aminopropan-2-ol was initially introduced. With stirring, the formalin solution was added such that a temperature of 70° C. was not exceeded. If necessary, cooling was carried out. This gave approx. 51% strength solutions of TTT in water.

Samples of this solution were stored in bottles made of polyethylene at −5° C., 25° C. and 40° C. in order to investigate the stability.

| Zero value | A | B |
|---|---|---|
| Appearance | clear, colourless | clear, colourless |
| Colour number Hazen/Gardner | 5/0.0 | 2/0.0 |
| Density g/ml at 20° C. | 1.0682 | 1.0662 |
| Refraction at 20° C. | 1.4252 | 1.4254 |
| Cleavable HCHO % | 17.1 | 16.6 |

| 6 weeks | A | | | B | | |
|---|---|---|---|---|---|---|
| | −5° C. | 25° C. | 40° C. | −5° C. | 25° C. | 40° C. |
| Appearance | clear, slightly yellowish | clear, pale yellow | clear, intense yellow | clear, slightly yellowish | clear, yellowish | clear, yellow |
| Colour number Hazen/Gardner | 7/0.0 | 54/0.2 | 704/3.9 | 4/0.0 | 12/0.0 | 150/0.7 |
| Cleavable HCHO | n.d. | 17.3% | 16.1% | n.d. | 16.6% | 16.3% |
| Decrease in HCHO | n.d. | 1.8% | 6.4% | n.d. | 0.0% | 2.4% |

|  | A | | | B | | |
|---|---|---|---|---|---|---|
| 3 months | −5° C. | 25° C. | 40° C. | −5° C. | 25° C. | 40° C. |
| Appearance | clear, yellowish | clear, yellow | clear, orange | clear, slightly yellowish | clear, yellowish | clear, yellow |
| Colour number Hazen/Gardner | n.d. | 154/0.9 | ***/7.0 | n.d. | 29/0.1 | 477/3.0 |
| pH | n.d. | 10 | 10 | n.d. | 10 | 10 |
| HCHO | n.d. | 16.6% | 14.4% | n.d. | 16.4% | 15.5% |
| Decrease in HCHO | | 2.9% | 15.8% | | 1.2% | 6.6% | n.d. = not determined.

Even after three months, considerable improvements are evident in the stability for a slight excess of MIPA, and the storage at 40° C. reveals the lack of longterm stability both in the colour and also as the content of cleavable formaldehyde drops.

Experiment 4

Samples of the following solutions were stored in bottles made of polyethylene at −5° C., 25° C. and 40° C. in order to investigate the stability. Parts by weight are given in the table below.

A:
MIPA and water were initially introduced. With stirring, paraformaldehyde was added such that a temperature of 70° C. was not exceeded. Then, stirring was carried out for approx. 1 h at 70° C. until paraformaldehyde had completely dissolved, and then the mixture was left to cool. This gave an approx. 40% strength TTT solution.

B:
Water was initially introduced and grotan WS was added with stirring. This gave an approx. 40% strength TTT solution.

C:
Water was initially introduced and Grotan® WS and MIPA were added with stirring.
This gave an approx. 40% strength TTT solution.

D:
Water was initially introduced and Grotan® WS and formaldehyde were added with stirring. This gave an approx. 40% strength TTT solution.

E:
MIPA and water were initially introduced. Formaldehyde (32%) was added with stirring such that a temperature of 70° C. was not exceeded. Cool. This gave an approx. 50% strength TTT solution.

|  | A | B | C | D | E |
|---|---|---|---|---|---|
| Demineralised Water | 48.75 | 50.00 | 48.26 | 47.83 | |
| 1-aminopropan-2-ol | 36.05 | | 1.74 | | 47.07 |
| Paraformaldehyde 91% | 15.20 | | | | |
| grotan ® WS | | 50.00 | 50.00 | 50.00 | |
| Formalin solution 32% | | | | 2.17 | 52.93 |
| Molar ratio HCHO/MIPA | 1:1.05 | 1:1 | 1:1.05 | 1.05:1 | 1:1.11 |

| Zero value | A | B | C | D | E |
|---|---|---|---|---|---|
| Appearance | clear, yellowish | clear, yellow | clear, yellow | clear, yellow | clear, yellowish |
| Colour number Hazen/Gardner | 11/0.1 | 65/0.2 | 71/0.3 | 60/0.2 | 5/0.0 |
| Density g/ml at 20° C. | 1.0555 | 1.0545 | 1.0554 | 1.0555 | 1.0652 |
| Refraction at 20° C. | 1.4054 | 1.4033 | 1.4061 | 1.4037 | 1.4277 |
| Cleavable HCHO | 13.2% | 13.3% | 13.3% | 13.7% | 16.0% |

| 1st month 5° C. | A | B | C | D | E |
|---|---|---|---|---|---|
| Appearance | clear, yellowish | clear, yellow | clear, yellow | clear, yellow | clear, yellowish |

| 1st month 25° C. | A | B | C | D | E |
|---|---|---|---|---|---|
| Appearance | clear, yellowish | clear, yellow | clear, yellow | clear, yellow | clear, yellowish |
| Colour number Hazen/Gardner | 26/0.1 | 160/0.8 | 236/1.2 | 140/0.6 | 96/0.3 |

| 1st month 40° C. | A | B | C | D | E |
|---|---|---|---|---|---|
| Appearance | clear, yellow | clear, intense yellow | clear, intense yellow | clear, dark yellow-pale orange | clear, pale yellow |
| Colour number Hazen/Gardner | 303/1.8 | 763/4.0 | 499/3.1 | ***/5.8 | 96/0.3 |
| Cleavable HCHO | 12.8% | 12.4% | 12.8% | 12.1% | 15.8% |
| Remaining HCHO | 97% | 93.2% | 96.2% | 88.8% | 98.75% |

Thus, whereas an aqueous dilution of TTT (experiment B) is insufficiently storage-stable, this lack of stability is yet even further intensified with an excess of formaldehyde (experiment D). By contrast, a content of MIPA which exceeds the stoichiometric amount (as is present in TTT) improves the stability of the solutions, specifically if i) TTT is prepared in situ and then the excess of MIPA remains (experiment A), and also if ii) TTT has been provided in the form of the commercial product Grotan® WS and has been admixed with a small amount of MIPA (experiment C). A higher excess of MIPA further improves the storage stability (experiment E).

Experiment 5

Solutions with different contents of grotan WS were prepared and it was investigated whether the stabilization according to the invention is achieved at the different concentrations of TTT. The table below gives the parts by weight.

|                    | A     | B      | C     | D      |
|--------------------|-------|--------|-------|--------|
| grotan ® WS        | 30    | 30     | 50    | 50     |
| Demineralised water| 70    | 68.26  | 50    | 48.26  |
| 1-aminopropan-2-ol |       | 1.74   |       | 1.74   |

| Zero value | A | B | C | D |
|---|---|---|---|---|
| Appearance | clear, pale yellow | clear, pale yellow | clear, pale yellow | clear, pale yellow |
| Colour number Hazen/Gardner | 48/0.2 | 51/0.2 | 80.03 | 77/0.3 |
| Density g/ml at 20° C. | 1.0306 | 1.0316 | 1.0543 | 1.0554 |
| Refraction at 20° C. | 1.3738 | 1.3765 | 1.4031 | 1.4061 |
| pH | 10 | 11 | 10 | 11 |
| Cleavable HCHO | 7.81% | 7.81% | 13.1% | 13.1% |

Samples of these solutions were stored in bottles made of polyethylene at −5° C., 25° C. and 40° C. in order to test the stability.

|                | A | B | C | D |
|---|---|---|---|---|
| 1st month 25° C. | | | | |
| Appearance | clear, pale yellow | clear, pale yellow | clear, pale yellow | clear, pale yellow |
| 1st month 40° C. | | | | |
| Appearance | clear, intense yellow | clear, yellow | clear, intense yellow | clear, yellow |

|                | A | B | C | D |
|---|---|---|---|---|
| Cleavable HCHO decrease relative to the zero value | 7.2%<br>7.8% | 7.69%<br>1.5% | 12.4%<br>5.3% | 12.8%<br>2.3% |

| 1st month 60° C. | A | B | C | D |
|---|---|---|---|---|
| Appearance | clear, dark red | clear, red | clear, dark red | clear, red |
| Cleavable HCHO decrease relative to the zero value | 1.99%<br>74.5% | 4.63%<br>40.7% | 5.31%<br>59.5% | 10.0%<br>23.7% |

Experiment 6

It was also investigated whether the stabilization achieved according to the invention with the particularly preferred agent MIPA is also achieved with other alkalizing agents. Parts by weight are given in the table below.

|                        | A  | B     | C     | D     | E     | F     | G     |
|---|---|---|---|---|---|---|---|
| grotan WS ®            | 50 | 50    | 50    | 50    | 50    | 50    | 50    |
| Demineralised water    | 50 | 48.26 | 48.26 | 48.26 | 48.26 | 48.26 | 48.26 |
| 1-aminopropan-2-ol     |    | 1.74  |       |       |       |       |       |
| NaOH 45%               |    |       | 1.74  |       |       |       |       |
| Triethanolamine        |    |       |       | 1.74  |       |       |       |
| Ammonia 25%            |    |       |       |       | 1.74  |       |       |
| Ethanolamine           |    |       |       |       |       | 1.74  |       |
| N,N-bis(3-aminopropyl) dodecylamine | |  |  |  |  |  | 1.74 |

| Zero value | A | B | C | D | E | F | G |
|---|---|---|---|---|---|---|---|
| Appearance | clear, yellow | clear, yellow | clear, yellow | clear, yellow | clear, yellow | clear, yellow | cloudy, milky, inhomo-geneous |
| Colour number Hazen/Gardner | 81/0.3 | 87/0.3 | 177/0.9 | 82/0.3 | 98/0.4 | 88/0.4 | n.d. |
| Density g/ml at 20° C. | 1.0547 | 1.0556 | 1.0634 | 1.0577 | 1.0540 | 1.0565 | n.d. |
| Refraction at 20° C. | 1.4036 | 1.4064 | 1.4062 | 1.4065 | 1.4043 | 1.4064 | n.d. |
| pH | 9 | 9 | 12 | 9 | 9 | 9 | n.d. |
| Cleavable formaldehyde, % | 13.3 | 13.3 | 13.3 | 13.3 | 13.3 | 13.3 | n.d. | n.d. = not determined

Samples of the solutions were stored in bottles made of polyethylene at −5° C., 25° C. and 40° C. in order to investigate the stability.

| 1st month −5° C. | A | B | C | D | E | F |
|---|---|---|---|---|---|---|
| Appearance | clear, yellow | clear, yellow | clear, yellow | clear, yellow | clear, yellow | clear, yellow |

| 1st month 25° C. | A | B | C | D | E | F |
|---|---|---|---|---|---|---|
| Appearance | clear, yellow | clear, yellow | clear, intense yellow | clear, yellow | clear, yellow | clear, yellow |
| Colour number Hazen/Gardner | 188/0.9 | 203/1.1 | 988/4.7 | 192/1.0 | 177/0.9 | 216/1.1 |

| 1st month 40° C. | A | B | C | D | E | F |
|---|---|---|---|---|---|---|
| Appearance | clear, intense yellow | clear, intense yellow | clear, dark yellow/pale orange yellow | clear, intense yellow | clear, intense yellow | clear, intense yellow |
| Colour number Hazen/Gardner | ***/4.8 | 635/3.7 | ***/8.8 | 983/4.7 | 447/2.6 | 560/3.4 |
| Cleavable formaldehyde | 12.2% | 12.8% | 11.7% | 12.3% | 12.9% | 12.9% |

Thus, whereas the TTT dilution A is not storage-stable, this instability is yet even further intensified by sodium hydroxide solution (experiment C) and triethanolamine (an alkanolamine without primary amino group), experiment D. N,N-bis(3-aminopropyl)-dodecylamine (an alkylamine with alkyl group having more than 8 carbon atoms) even immediately triggers an inhomogeneity, the alkylamine is thus incompatible with TTT and the experiment was terminated. By contrast, it is possible according to the invention to formulate dilute TTT solutions with MIPA (experiment B), ammonia solution (experiment E) or ethanolamine (experiment F).

Experiment 7

It was also investigated with what amounts of component b) a stabilization is achieved according to the invention (the table below gives parts by weight):

| | A | B | C | D | E | F |
|---|---|---|---|---|---|---|
| grotan WS ® | 50.00 | 50.00 | 50.00 | 50.00 | 50.00 | 50.00 |
| Water | 50.00 | 49.65 | 49.30 | 48.25 | 46.50 | 43.00 |
| 1-amino propan-2-ol | | 0.35 | 0.70 | 1.75 | 3.50 | 7.00 |
| Excess of MIPA, parts by weight based on 100 parts by weight of TTT | 0 | 0.875 | 1.75 | 4.375 | 8.75 | 17.5 |
| Zero value | | | | | | |
| Appearance | clear, yellow | clear, yellow | clear, yellow | clear, yellow | clear, yellow | clear, yellow |
| Colour number Hazen/Gardner | 74/0.3 | 78/0.3 | 80/0.3 | 80/0.3 | 94/0.8 | 94/0.5 |
| Density g/ml at 20° C. | 1.0544 | 1.0548 | 1.0548 | 1.0554 | 1.0558 | 1.0563 |
| Refraction at 20° C. | 1.4031 | 1.404 | 1.4043 | 1.4062 | 1.4088 | 1.4139 |
| Ph | 10 | 10 | 10-11 | 11 | 11-12 | 12 |
| Cleavable HCOH | 13.1 | 13.1 | 13.1 | 13.1 | 13.1 | 13.1 |

Samples of these solutions were stored in bottles made of polyethylene at 25° C. and 40° C. in order to investigate the stability.

| 1 month 25° C. | A | B | C | D | E | F |
|---|---|---|---|---|---|---|
| Appearance | clear, yellow | clear, yellow | clear, yellow | clear, yellow | clear, yellow | clear, yellow |

| 1 month 60° C. | A | B | C | D | E | F |
|---|---|---|---|---|---|---|
| Appearance | clear, red | clear, red | clear, red | clear, red | clear, red | clear, orange with brown tinge |
| Cleavable HCHO | 3.57% | 3.79% | 4.39% | 6.03% | 6.93% | 9.92% |
| decrease relative to the zero value | 72.7% | 71.1% | 66.5% | 54.0% | 47.1% | 24.3% |

In each case based on 100 parts by weight of TTT: whereas it is not possible with less than one part by weight of MIPA (experiment B) to stabilize TTT, the stabilization according to the invention is present for an amount of more than one part by weight of MIPA (experiment C), and significantly more marked for an even larger amount (experiment D), greater with more than five parts by weight of MIPA (experiment E), and then even greater with more than ten parts by weight of MIPA (experiment F). Consequently, it is demonstrated that the stabilization according to the invention is also possible with comparatively small amounts of MIPA.

Experiment 8

It was investigated whether the stabilization achieved according to the invention is also observed in the presence of further ingredients which are often used together with TTT. The table below gives parts by weight.

| | A | B | C |
|---|---|---|---|
| Demineralised water | 47.75 | 47.74 | 44.75 |
| grotan WS ® | 42.25 | 42.25 | 42.25 |
| 2-Hydroxy propylamine | — | — | 3 |
| Glucopon 215 UP (62-65%) | 5 | 5 | 5 |
| Monoethylene glycol | 5 | 5 | 5 |
| BHT | — | 0.01 | — |
| Zero value | | | |
| Appearance | slightly opaque, pale yellow | slightly opaque, pale yellow | slightly opaque, pale yellow |
| Colour number Hazen/Gardner | 5810.2 | 58/0.3 | 73/0.4 |
| Density g/ml at 20° C. | 1.0595 | 1.0597 | 1.0610 |
| Refraction at 20° C. | 1.4028 | 1.4028 | 1.4079 |
| Cleavable HCHO | 11.0% | 11.1% | 11.2% |
| 1st month −5° C. | | | |
| Appearance | slightly opaque, pale yellow | slightly opaque, pale yellow | slightly opaque, pale yellow |
| 1st month 25° C. | | | |
| Appearance | slightly cloudy, yellow | slightly cloudy, pale yellow | slightly cloudy, pale yellow |
| Colour number Hazen/Gardner | 128/0.6 | 124/0.7 | 178/1.0 |
| Cleavable HCHO % | 10.9% | 11.2% | 11.2% |
| 1st month 40° C. | | | |
| Appearance | slightly cloudy, yellow | slightly cloudy, yellow | slightly cloudy, yellow |
| Colour number Hazen/Gardner | 945/4.6 | 901/4.5 | 412/2.6 |
| Cleavable HCHO | 10.6% | 10.5% | 11.2% |
| decrease relative to the zero value | 3.6% | 5.4% | 0% |
| 3rd month 25° C. | | | |
| Appearance | clear, yellow | clear, yellow | clear, yellow |
| Cleavable HCHO | 10.8% | 10.9% | 11.1% |
| decrease relative to the zero value | 1.8% | 1.8% | 0.9% |

-continued

| | A | B | C |
|---|---|---|---|
| 3rd month 40° C. | | | |
| Appearance | clear, orange | clear, orange | clear, dark yellow |
| Cleavable HCHO | 9.24% | n.d. | 11.1% |
| decrease relative to the zero value | 16% | n.d. | 0.9% | n.d. = not determined.

It is thus demonstrated that the stabilization according to the invention of TTT is also observed in the presence of for example a nonionic surfactant, and specifically without the presence of the nonionic surfactant being obligatory (in contrast to the teaching of EP 0 347 815 A2).

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

The invention claimed is:

1. A preparation which comprises:
   a) 10% to 80% by weight of α,α',α''-trimethyl-1,3,5-triazine-1,3,5-(2H,4H,6H)triethanol (TTT) and
   b) one or more additives selected from
      (i) Ammonia,
      (ii) Alkanolamines with primary amino group and alkyl group having at most eight carbon atoms, and/or
      (iii) Alkylamines with primary amino group and alkyl group having at most eight carbon atoms,
   wherein the weight ratio a)/b) is in the range from 100:25 to 100:1.

2. The preparation according to claim 1, characterized in that the fraction a) of α,α',α''-trimethyl-1,3,5-triazine-1,3,5-(2H,4H,6H)triethanol is 13 to 75% by weight.

3. The preparation according to claim 2, characterized in that the fraction a) of α,α',α''-trimethyl-1,3,5-triazine-1,3,5-(2H,4H,6H)triethanol is 16 to 70% by weight.

4. The preparation according to claim 1, characterized in that component b) comprises one or more additives selected from
   (i) Ammonia, and/or
   (ii) Alkanolamines with primary amino group and alkyl group having at most eight carbon atoms.

5. The preparation according to claim 1, characterized in that component b) is ammonia.

6. The preparation according to claim 1, characterized in that component b) consists of one or more alkanolamines, selected from isopropanolamine, propanolamine, monoethanolamine, aminomethylpropanol and aminobutanol.

7. The preparation according to claim 1, characterized in that component b) is 1-aminopropan-2-ol (isopropanolamine).

8. A preparation which comprises:
   a) 10% to 80% by weight of α,α',α''-trimethyl-1,3,5-triazine-1,3,5-(2H,4H,6H)triethanol (TTT) and
   b) one or more additives selected from
      (i) Ammonia,
      (ii) Alkanolamines with primary amino group and alkyl group having at most eight carbon atoms, and/or
      (iii) Alkylamines with primary amino group and alkyl group having at most eight carbon atoms,
   wherein the weight ratio a)/b) is in the range from 100:25 to 100:1.5.

9. The preparation according to claim 8, characterized in that the weight ratio a)/b) is in the range from 100:20 to 100:2.

10. The preparation according to claim 8, characterized in that the fraction a) of α,α',α''-trimethyl-1,3,5-triazine-1,3,5-(2H,4H,6H)triethanol is 13 to 75% by weight.

11. The preparation according to claim 10, characterized in that the fraction a) of α,α',α''-trimethyl-1,3,5-triazine-1,3,5-(2H,4H,6H)triethanol is 16 to 70% by weight.

12. The preparation according to claim 8, characterized in that component b) comprises one or more additives selected from
    (i) Ammonia, and/or
    (ii) Alkanolamines with primary amino group and alkyl group having at most eight carbon atoms.

13. The preparation according to claim 8, characterized in that component b) is ammonia.

14. The preparation according to claim 8, characterized in that component b) consists of one or more alkanolamines, selected from isopropanolamine, propanolamine, monoethanolamine, aminomethylpropanol and aminobutanol.

15. The preparation according to claim 8, characterized in that component b) is 1-aminopropan-2-ol (isopropanolamine).

\* \* \* \* \*